United States Patent [19]

Bastian

[11] 4,150,136
[45] Apr. 17, 1979

[54] BENZ[G]ISOQUINOLINES AND USE THEREOF

[75] Inventor: Jean-Michel Bastian, Therwil, Switzerland

[73] Assignee: Sandoz Ltd., Basel, Switzerland

[21] Appl. No.: 811,585

[22] Filed: Jun. 30, 1977

[30] Foreign Application Priority Data

Jul. 6, 1976 [CH]  Switzerland .................. 8631/76
Jul. 6, 1976 [CH]  Switzerland .................. 8632/76

[51] Int. Cl.$^2$ .................. A61K 31/47; C07D 217/24; C07D 217/02
[52] U.S. Cl. .................. 424/258; 546/101
[58] Field of Search ............ 260/283 R, 283 S, 289 C; 424/258

Primary Examiner—Donald G. Daus
Assistant Examiner—D. B. Springer
Attorney, Agent, or Firm—Gerald D. Sharkin; Robert S. Honor; Timothy G. Rothwell

[57] ABSTRACT

The present invention provides novel compounds of the formula,

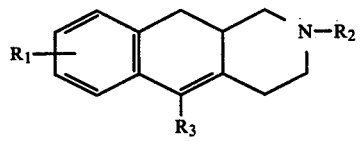

wherein $R_1$ is hydrogen, halogen, alkyl or alkoxy; $R_2$ may, for example, be hydrogen, alkyl, alkenyl, alkinyl or phenylalkyl, the phenyl ring of which may be mono-substituted with halogen, alkyl or alkoxy; and $R_3$ is hydrogen, alkyl, thienyl, phenyl or phenyl which may be mono- or di-substituted with halogen, alkyl, alkoxy or alkylthio, useful, for example, as anti-depressants and analgesics.

17 Claims, No Drawings

BENZ[G]ISOQUINOLINES AND USE THEREOF

The present invention relates to benz[g]isoquinoline derivatives.

More particularly, the present invention provides compounds of formula I,

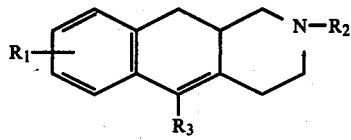

wherein $R_1$ is hydrogen, halogen of atomic number from 9 to 35, alkyl of 1 to 4 carbon atoms or alkoxy of 1 to 4 carbon atoms, $R_2$ is hydrogen; alkyl of 1 to 6 carbon atoms; alkenyl of 3 to 6 carbon atoms or alkinyl of 3 to 6 carbon atoms, the multiple bonds of which are not adjacent to the nitrogen atom of the tricyclic ring system; hydroxyalkyl of 2 to 5 carbon atoms, the hydroxy group of which is separated by at least two carbon atoms from the nitrogen atom; alkylcarbonylalkyl of 3 to 5 carbon atoms; or phenylalkyl of 7 to 10 carbon atoms, the phenyl ring of which may be mono-substituted with halogen of atomic number from 9 to 35, alkyl of 1 to 4 carbon atoms or alkoxy of 1 to 4 carbon atoms, and $R_3$ is hydrogen; alkyl of 1 to 4 carbon atoms; thienyl; phenyl or phenyl mono- or di-substituted with halogen of atomic number from 9 to 35, alkyl of 1 to 4 carbon atoms, alkoxy of 1 to 4 carbon atoms or alkylthio of 1 to 4 carbon atoms.

$R_1$ is preferably hydrogen. When $R_1$ is halogen, this is preferably chlorine. When $R_1$ is alkyl, this is preferably ethyl or methyl, especially methyl. When $R_1$ is alkoxy, this is preferably ethoxy or methoxy, especially methoxy. $R_1$ is preferably in the 7- or 8-position of the tricyclic ring system.

$R_2$ is preferably hydrogen. When $R_2$ is alkyl, this is preferably isopropyl or methyl. When $R_2$ is alkenyl or alkinyl, these preferably contain 3 or 4 carbon atoms. When $R_2$ is hydroxyalkyl, this preferably contains 2 or 3 carbon atoms. When $R_2$ is alkylcarbonylalkyl, this preferably contains an acetyl group and especially signifies acetonyl. When $R_2$ is phenylalkyl, this is preferably benzyl. When the phenyl substituted with halogen, the substituent is preferably chlorine. When the phenyl ring is substituted with alkyl, the substituent is preferably ethyl or methyl, especially methyl. When the phenyl ring is substituted with alkoxy, the substituent is preferably ethoxy or methoxy, especially methoxy.

$R_3$ is preferably hydrogen. Another preferred group is alkyl, preferably ethyl or methyl, especially methyl. A further preferred group is unsubstituted phenyl. In one group of compounds, $R_3$ is thienyl. When $R_3$ is phenyl, this may be mono- or di-substituted with halogen of atomic number from 9 to 35, alkyl of 1 to 4 carbon atoms, alkoxy of 1 to 4 carbon atoms or alkylthio of 1 to 4 carbon atoms. When the phenyl substituent is halogen, this is preferably chlorine. When the phenyl substituent is alkyl, this is preferably ethyl or methyl, especially methyl. When the phenyl substituent is alkoxy, this is preferably ethoxy or methoxy, especially methoxy. When the phenyl substituent is alkylthio, this is preferably ethylthio or methylthio, especially methylthio.

The invention further provides a process for the production of a compound of formula I comprising
(a) producing a compound of formula Ia,

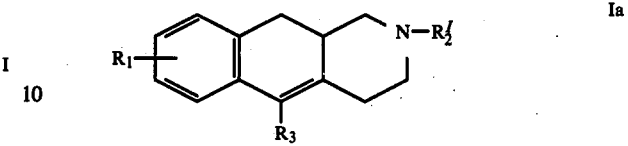

wherein
$R_1$ and $R_3$ are as previously defined, and
$R_2^I$ is hydrogen; alkyl of 1 to 6 carbon atoms; alkenyl of 3 to 6 carbon atoms, the double bond of which is not adjacent to the nitrogen atom of the tricyclic ring system; phenylalkyl of 7 to 10 carbon atoms, the phenyl group of which may be mono-substituted with halogen of atomic number from 9 to 35, alkyl of 1 to 4 carbon atoms or alkoxy of 1 to 4 carbon atoms, with the proviso that $R_2^I$ can only be hydrogen when $R_3$ is hydrogen, by removing water from a compound of formula II,

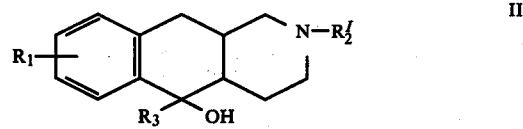

wherein $R_1$, $R_2^I$ and $R_3$ are as previously defined,
(b) producing a compound of formula Ib,

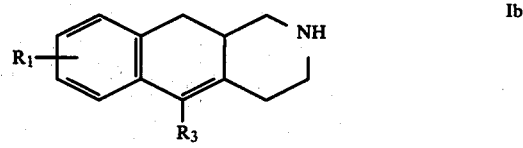

wherein $R_1$ and $R_3$ are as previously defined, by removal of a residue $R_4$ from a compound of formula III,

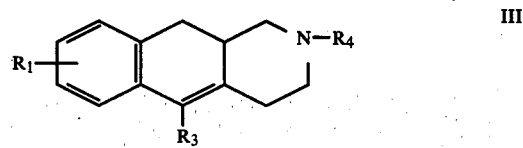

wherein $R_1$ and $R_3$ are as previously defined, and $R_4$ is a residue which can be removed solvolytically, or
(c) producing a compound of formula Ic,

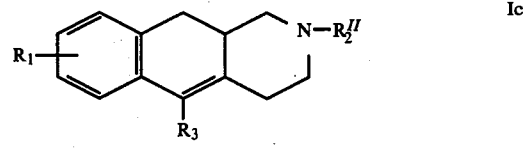

wherein $R_1$ and $R_3$ are as previously defined, and $R_2^{II}$ has the same significance as $R_2$ except that $R_2^{II}$ may not signify hydrogen, by alkylating a compound of formula Ib, as previously defined.

Process variant (a) can be effected by known methods for the removal of water from carbinols, for example by reaction with a suitable water removing agent. The reaction may be effected in the presence of an inert organic solvent such as a lower alcohol.

Process variant (b) can be effected by known methods for the removal of amino protecting groups from heterocyclic amines. The removal is usually effected solvolytically, especially hydrolytically, for example by known methods for the cleaving of urethanes.

Process variant (c) can be effected by the usual methods for alkylating secondary amines. For example, the compound of formula Ib can be reacted with a compound of formula IV, $$R_2{}^{II}\text{-}X \qquad\qquad IV$$

wherein $R_2{}^{II}$ is as previously defined and X is an acidic residue of a reactive ester. Preferably X is halogen or an organic sulphonic acid residue. The reaction may be effected in manner analogous to known methods. When $R_2{}^{II}$ is an alkanoylalkyl group as previously defined, the compounds of formula Ic can also be produced by the addition of an appropriate $\alpha,\beta$-unsaturated ketone to the appropriate compound of formula Ib, in manner analogous to known methods. The compounds of formula Ic wherein $R_2{}^{II}$ is hydroxyalkyl, as previously defined, can be prepared from the appropriate epoxide.

The resulting compounds of formula I may be isolated and purified using conventional techniques.

Free base forms of the compounds of formula I may be converted into acid addition salt forms and vice versa in conventional manner.

The starting materials of formula II wherein $R_3$ is other than hydrogen can, for example, be produced in known manner from the product of the reaction between a compound of formula V,

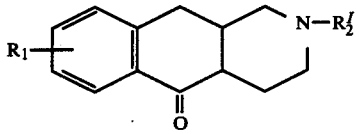

wherein $R_1$ and $R_2{}^{I}$ are as previously defined, and an appropriate Grignard reagent.

The compounds of formula II wherein $R_3$ is hydrogen can be obtained from compounds of formula VI,

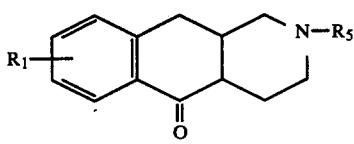

wherein $R_1$ is as previously defined and $R_5$ is hydrogen, carbalkoxy, alkyl, alkenyl or phenylalkyl as previously defined, by reducing the keto group to a hydroxy group and, when appropriate, removing the carbalkoxy group.

The compounds of formulae V and VI can be prepared according to known methods from compounds of formula VII,

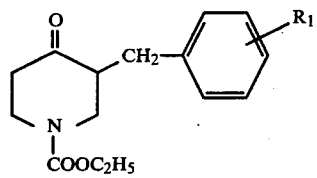

wherein $R_1$ is as previously defined, for example, as described in Example 1, steps (a) to (h).

The compounds of formula III can, for example, be obtained from compounds of formula I in which $R_2$ is methyl by substituting the methyl group with a solvolytically removable residue, e.g. by reaction with a halogen derivative of a residue $R_4$ such as chloroformic acid esters of bromocyanogen. Compounds of formula III wherein $R_3$ is hydrogen and $R_4$ is carbalkoxy can also be prepared by removal of water from the appropriate 5-hydroxy derivative in manner analogous to process variant (a).

Insofar as the production of starting materials is not described, these are either known or may be produced in accordance with known processes or in manner analogous to the processes described herein, or to known processes.

In the following non-limitative Examples, all temperatures are indicated in degrees Celsius.

EXAMPLE 1:
1,2,3,4,10,10a-Hexahydro-2-isopropyl-5-phenylbenz[g]isoquinoline

[Process variant (a)]

5.9 g of crude trans-1,2,3,4,4a,10a-hexahydro-2-isopropyl-5-phenyl-10H-benz[g]isoquinoline-5-ol are dissolved in 180 ml of isopropanol and 36 ml of 7 N isopropanolic hydrochloric acid solution, boiled for 2 hours and concentrated by evaporation. Water is added to the residue; the latter is made alkaline with concentrated caustic soda solution and is extracted with methylene chloride. The extracts are washed with water, dried, and concentrated by evaporation, and the remaining title compound is converted in isopropanol to the fumarate form. M.P. 199°–200°.

The starting material is produced as follows:
(a) 15.6 g of acetone cyanohydrin are added to 47.5 g of 3-benzyl-4-oxopiperidine-1-carboxylic acid ethyl ester and after the addition of a spatula tipful of potassium carbonate moistened with methanol, the reaction mixture is stirred for 5–8 hours at room temperature. After allowing the mixture to stand for 5–10 hours at room temperature, 20 ml of ether and 20 ml of petroleum ether are added to the semi-liquid reaction mixture; the solid product is filtered by suction, washed and dried at 50°. M.P. of the resulting 3-benzyl-4-cyano-4-hydroxypiperidine-1-carboxylic acid ethyl ester: 120°–121° (from ether/petroleum ether).

(b) 6.5 ml of thionyl chloride are added dropwise to a solution of 16.0 g of the above product in 20 ml of anhydrous pyridine and 14 ml of anhydrous benzene at 5°. The reaction mixture is allowed to stand for 5 hours at 0° to 5° and for 2 hours at room temperature and poured onto 100 ml of ice/water. The organic phase is separated and washed neutral with water, dried over magnesium sulphate and concentrated by evaporation. The mixture of 5- benzyl-4-cyano-1,2,3,6-tetrahydropyridine-1-carboxylic acid ethyl ester and 3-benzyl-4-cyano-1,2,5,6-tetrahydropyridine-1-carboxylic acid ethyl ester obtained as an oil is further worked up in crude form.

(c) A solution of 20.0 g of the above mixture in 300 ml of ethyl acetate is hydrogenated in the presence of 2.0 g of 10% palladium/charcoal at a hydrogen pressure of 30 atm and room temperature. After take-up of the theoretical amount of hydrogen, the catalyst is filtered off and the solvent is concentrated by evaporation under reduced pressure. The 3-benzyl-4-cyanopiperidine-1-carboxylic acid ethyl ester (cis-trans isomeric mixture), obtained as an oil, is further worked up in crude form.

(d) 99.7 ml of 40% hydrogen peroxide solution are added to a solution of 20.0 g of the above product in 400 ml of acetone and 30 ml of 2N sodium carbonate solution and the mixture is stirred for 2 days at room temperature. The acetone is subsequently concentrated by evaporation, the residue diluted with water and extracted with methylene chloride. After washing with sodium carbonate solution and water, the organic solutions are dried over sodium sulphate and concentrated by evaporation. The residue is fractionally crystallized from ether, whereupon trans-3-benzyl-4-carbamoyl-piperidine-1-carboxylic acid ethyl ester having a M.P. of 155°–156° first crystallizes, followed by the cis-isomer having a M.P. of 136°–138°.

(e) 20 g of the above product are boiled with 120 ml of concentrated hydrochloric acid and 240 ml of water for 4 hours, cooled to room temperature and extracted with methylene chloride. The extracts are washed with water, dried over magnesium sulphate and concentrated by evaporation, and the remaining 1-ethoxycarbonyl-3-benzyl-4-piperidine-carboxylic acid (cis-trans-isomeric mixture) is recrystallized from acetone/hexane. M.P. 143°–148°.

(f) A mixture of 20 g of the above product and 120 g of polyphosphoric acid is heated for one hour at 80°, poured onto ice/water and extracted several times with benzene. The organic solutions are washed with water, dried over magnesium sulphate and concentrated by evaporation. The remaining trans-1,2,3,4,4a,10a-hexahydro-5-oxo-10H-benz[g]isoquinoline-2-carboxylic acid ethyl ester is crystallized from ether. M.P. 90°–92°.

(g) A mixture of 15.0 g of the above product and 95 ml of acetic acid and 36.5 ml of 48% hydrobromic acid is boiled for 3.5 hours, cooled and made alkaline with concentrated caustic soda solution. The product obtained as an oil is extracted with methylene chloride; the organic solutions are washed with water, dried over potassium carbonate and concentrated by evaporation. The remaining trans-1,2,3,4,4a,10a-hexahydro-10H-benz[g]isoquinoline-5-one is recrystallized from acetone. M.P. of the hydrochloride: from 290° (decomposition).

(h) A mixture of 18.0 g of the above product, 20.0 g of sodium carbonate and 0.2 g of sodium iodide in 180 ml of dimethyl formamide is preheated to 50°. To this suspension are added dropwise 16.5 g of isopropyl bromide in 50 ml of dimethyl formamide over a period of 2 hours; the reaction mixture is stirred for 3.5 hours at the same temperature, cooled and poured onto ice/water. The organic substance is extracted with ether, the extracts are washed with water, dried over potassium carbonate and concentrated by evaporation. The remaining trans-1,2,3,4,4a,10a-hexahydro-2-isopropyl-10H-benz[g]isoquinoline-5-one is further worked up in crude form.

(i) Phenyllithium is produced from 0.77 g of lithium and 7.2 g of bromobenzene in 50 ml of anhydrous ether. After the lithium has been dissolved, a solution of 4.8 g of the above product in 70 ml of anhydrous ether is added dropwise at 10°–15°. The reaction mixture is stirred for one hour at room temperature and then refluxed for 18 hours with stirring. Water is added under strong cooling at approximately 0° to 10°, while stirring thoroughly, and the organic phase is separated. The latter is washed with water, dried over sodium sulphate and concentrated by evaporation. The remaining trans-1,2,3,4,4a,10a-hexahydro-2-isopropyl-5-phenyl-10H-benz[g]isoquinoline-5-ol is further worked up in crude form.

The following compounds of formula Ia can be obtained in manner analogous to that of Example 1, employing the appropriate compound of formula II in approximately equivalent amounts.

| Ex. No. | $R_1$ | $R_2$ | $R_3$ | M.P. |
|---|---|---|---|---|
| 2 | H | H | H | Decomp. from 250° (Hydrochloride) |
| 3 | H | —CH$_3$ | H | 240–242° (Hydrochloride) |
| 4 | H | " |  | 226–228° (Hydrogenfumarate) |
| 5 | H | i-C$_3$H$_7$ | —CH$_3$ | 247–249° (Hydrochloride) |
| 6 | H | —CH$_3$ | " | 238–239° (Hydrochloride) |
| 7 | H | " | —C$_2$H$_5$ | 238–240° (Hydrochloride) |
| 8 | H | " |  | 207–209° (Hydrochloride) |
| 9 | H | " |  | 138–140° (Base) |
| 10 | H | " |  | 132–134° (Base) |
| 11 | H | " |  | 254–256° (Hydrochloride) |
| 12 | H | i-C$_3$H$_7$ | " | 237–239° (Hydrochloride) |
| 13 | H | " |  | 245–247° (Hydrochloride) |
| 14 | H | " | H | 225–226° (Hydrochloride) |
| 15 | 7-CH$_3$ | —CH$_3$ | " | 246–247° (Hydrochloride) |
| 16 | 7-CH$_3$ | H | " | 263°(Decomp.) (Hydrochloride) |

EXAMPLE 17:
1,2,3,4,10,10a-Hexahydrobenz[g]isoquinoline

[Process variant (b)]

A mixture of 10 g of 1,2,3,4,10,10a-hexahydrobenz[g]isoquinoline-2-carboxylic acid ethyl ester in 100 ml of glacial acetic acid and 40 ml of 48% hydrobromic acid is boiled for 3 to 4 hours, concentrated and, under cooling, made alkaline with concentrated caustic soda. The mixture is extracted with methylene chloride, the extracts washed with water and dried over sodium sulphate. The solvent is evaporated and the title compound, which remains as an oily residue, is converted to the hydrochloride form in ethanol. M.P. 250° (decomp.).

The starting material can be prepared as follows:

(a) 20.0 g of trans-1,2,3,4,4a,10a-hexahydro-5-oxo-10H-benz[g]isoquinoline-2-carboxylic acid ethyl ester [prepared as in Example 1, steps (a) to (f)] are dissolved in 110 ml of 95% ethanol and preheated to 40°. A solution of 7.0 g of sodium borohydride in 32.5 ml of water and 2 ml of concentrated caustic soda is added dropwise at this temperature. The reaction solution is stirred for 2 hours at the same temperature, boiled for 30 minutes, cooled and evaporated to dryness. The residue is partitioned between chloroform and water; the organic layer is separated, washed with water, dried over sodium sulphate and evaporated. The residue, trans-1,2,3,4,4a,10a-hexahydro-5-hydroxy-10H-benz[g]isoquinoline-2-carboxylic acid ethyl ester, is used for the next step without further purification.

(b) 15.0 g of the aforementioned product are taken up in 200 ml of 5N hydrogen chloride in isopropanol, stirred at 40° to 50° for 15 hours and evaporated. The residue is partitioned between water and methylene chloride, the organic layer separated, washed with water, dried over sodium sulphate and evaporated. The crude residue, 1,2,3,4,10,10a-hexahydrobenz[g]isoquinoline-2-carboxylic acid ethyl ester is used directly for the last step.

EXAMPLE 18:
1,2,3,4,10,10a-Hexahydro-2-isopropyl-5-phenylbenz[g]isoquinoline [Process variant (c)]

A mixture of 22.0 g of 1,2,3,4,10,10a-hexahydro-5phenylbenz[g]isoquinoline, 20.0 g of sodium carbonate and 0.2 g of sodium iodide in 180 ml of dimethylformamide are preheated to 50°. 16.5 g of isopropylbromide in 50 ml of dimethylformamide are added dropwise to the suspension over a 2 hour period, the reaction mixture further stirred for 3.5 hours at the same temperature, cooled and poured onto ice/water. The organic substance is extracted with benzene, the extracts washed with water, dried over sodium sulphate and evaporated and the title compound which remains converted to the fumarate form in isopropyl. M.P. 199°–200°.

The compounds of Examples 3 to 15 can be obtained in manner analogous to that of Example 18 by alkylation of the appropriate compound of formula Ib.

The compounds of formula I are useful because they possess pharmacological activity in animals. In particular, the compounds possess anti-depressant activity, as indicated in standard tests in animals, for example the tetrabenazine antagonism test of G. Stille [Arz. Forsch. 14, 534–7 (1964)] in which an antagonism of ptosis and catalepsy induced by tetrabenazine is observed. The compounds are administered i.p. at dosages of from about 20 to about 100 mg/kg of animal body weight. The compounds of formula I exhibit an oxotremorine-antagonism in mice and inhibit, for example, tremor and hypothermia caused by oxotremorine at doses of from about 20 to about 200 mg/kg s.c. of animal body weight.

The compounds are therefore useful as antidepressants, particularly for the treatment of endogenous and reactive depression and retarded depression.

For this use, the dosage will, of course, vary depending on the compound employed, mode of administration and treatment desired. However, in general, satisfactory results are obtained when administered at a daily dosage of from about 0.1 to 100 mg/kg of animal body weight, conveniently given in divided doses 2 to 4 times a day or in sustained release form. For the larger mammals, the total daily dosage is in the range of from about 5 to about 500 mg, and dosage forms suitable for oral administration comprise from about 1.5 mg to about 250 mg of the compounds admixed with a solid or liquid pharmaceutical carrier or diluent.

The compounds are also useful as analgesic agents for the treatment of pain, as indicated in standard tests, for example in the Tail Flick Test in mice on p.o. administration of from about 3 to 30 mg/kg of animal body weight, as well as by the inhibition of the phenylbenzoquinone syndrome in mice on p.o. administration of from about 3 to about 30 mg/kg of animal body weight.

For this use, the dosage will, of course, vary depending on the compound employed, mode of administration and treatment desired. However, in general, satisfactory results are obtained when administered at a daily dosage of from about 0.7 to about 30 mg/kg of animal body weight, conveniently given in divided doses 2 to 4 times a day or in sustained release form. For the larger mammals, the total daily dosage is in the range of from about 50 to about 250 mg, and dosage forms suitable for oral administration comprise from about 12 to about 125 mg of the compounds admixed with a solid or liquid pharmaceutical carrier or diluent.

The compounds of formula I wherein $R_3$ is hydrogen or alkyl are also useful as anti-aggressive agents for the treatment of aggressive behaviour, for example for the sedation of psychopaths and mentally retarded patients, as indicated in standard tests, for example in that according to the method of H.C.Y. Yen et al. [J. Pharmacol. Exp. Ther. 122, 85A (1958)] involving the aggression of mice induced by isolation, on p.o. administration of from about 3 to about 100 mg/kg of animal body weight.

For this use, the dosage will, of course, vary depending on the compound employed, mode of administration and treatment desired. However, in general, satisfactory results are obtained when administered at a daily dosage of from about 0.3 to about 100 mg/kg of animal body weight, conveniently given in divided doses 2 to 4 times a day or in sustained release form. For the larger mammals, the total daily dosage is in the range of from about 20 to about 200 mg, and dosage forms suitable for oral administration comprise from about 5 to about 100 mg of the compounds admixed with a solid or liquid pharmaceutical carrier or diluent.

Furthermore, at higher doses, the compounds of formula I wherein $R_3$ is hydrogen or alkyl are also useful as sedatives by virtue of their effect on the central nervous system, as indicated in standard tests, for example in the climbing test in mice on p.o. administration of from about 20 to about 200 mg/kg of animal body weight. Owing to their effect on the central nervous system, the compounds may be used in the psychiatric treatment of agitation.

For this use, the dosage will, of course, vary depending on the compound involved, mode of administration and treatment desired. However, in general, satisfactory results are obtained when administered at a daily dosage of from 0.3 to 200 mg/kg of animal body weight, conveniently given in divided doses 2 to 4 times a day or in sustained release form. For the larger mammals, the total daily dosage is in the range of from about 20 to about 200 mg, and dosage forms suitable for oral administration comprise from about 5 to about 100 mg of the compounds admixed with a solid or liquid pharmaceutical carrier or diluent.

The compounds of formula I wherein $R_3$ is thienyl, phenyl or substituted phenyl are also useful as blood platelet aggregation inhibitor agents, for example in the treatment or prophylaxis of thrombosis and for improving micro-circulation in animals, as indicated by an inhibition of blood platelet aggregation induced by adenosine diphosphate in rabbit platelet-rich plasma in accordance with the turbidimetric method of Born at a concentration of from about 1 to about 100 mg/kg of the compounds.

For the above-mentioned use, the dosage will, of course, vary depending on the compound employed, mode of administration and treatment desired. However, in general, satisfactory results are obtained when administered at a daily dosage of from about 0.1 to about 25 mg/kg of animal body weight, conveniently given in divided doses 2 to 4 times a day or in sustained release form. For the larger mammals, the total daily dosage is in the range of from about 10 to about 500 mg, and dosage forms suitable for oral administration comprise from about 2 to about 250 mg of the compounds admixed with a solid or liquid pharmaceutical carrier or diluent.

The compounds of formula I may be administered in pharmaceutically acceptable acid addition salt forms. Such forms exhibit the same order of activity as the free base forms and are readily prepared in conventional manner. Representative acids for acid addition salt formation include hydrochloric, sulphuric, fumaric, maleic and malonic acids. The present invention also provides a pharmaceutical composition comprising a compound of formula I, in free base form or in the form of a pharmaceutically acceptable acid addition salt, in association with a pharmaceutically acceptable diluent or carrier. Such compositions may be in the form of, for example, a solution or capsule.

In one group of compounds, $R_1$ is as previously defined, $R_2$ is hydrogen; alkyl of 1 to 4 carbon atoms; alkenyl of 3 to 6 carbon atoms or alkinyl of 3 to 6 carbon atoms, the multiple bonds of which are not adjacent to the nitrogen atom of the tricyclic ring system; hydroxyalkyl of 2 to 5 carbon atoms, the hydroxy group of which is separated by at least two carbon atoms from the nitrogen atom; alkylcarbonylalkyl of 3 to 5 carbon atoms or phenylalkyl of 7 to 10 carbon atoms, the phenyl ring of which may be mono-substituted with halogen of atomic number from 9 to 35, alkyl of 1 to 4 carbon atoms or alkoxy of 1 to 4 carbon atoms and $R_3$ is hydrogen.

In a second group of compounds, $R_1$ is as previously defined, $R_2$ is hydrogen; alkyl of 1 to 6 carbon atoms; alkenyl of 3 to 6 carbon atoms or alkinyl of 3 to 6 carbon atoms, the multiple bonds of which are not adjacent to the nitrogen atom of the tricyclic ring system or phenylalkyl of 7 to 10 carbon atoms, the phenyl ring of which may be mono-substituted with halogen of atomic number from 9 to 35, alkyl of 1 to 4 carbon atoms or alkoxy of 1 to 4 carbon atoms and $R_3$ is alkyl of 1 to 4 carbon atoms; thienyl; phenyl or phenyl mono- or di-substituted with fluorine, chlorine, alkyl of 1 to 4 carbon atoms or alkoxy of 1 to 4 carbon atoms.

What is claimed is:

1. A compound of the formula

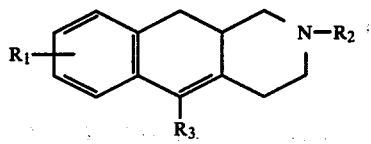

wherein
$R_1$ is hydrogen, halogen of atomic number from 9 to 35, alkyl of 1 to 4 carbon atoms or alkoxy of 1 to 4 carbon atoms, $R_2$ is hydrogen; alkyl of 1 to 6 carbon atoms; or alkenyl of 3 to 6 carbon atoms or alkinyl of 3 to 6 carbon atoms, the multiple bonds of which are not adjacent to the nitrogen atom of the tricyclic ring system; or phenylalkyl of 7 to 10 carbon atoms, the phenyl ring of which may be mono-substituted with halogen of atomic number from 9 to 35, alkyl of 1 to 4 carbon atoms or alkoxy of 1 to 4 carbon atoms, and $R_3$ is hydrogen; alkyl of 1 to 4 carbon atoms; phenyl or phenyl mono- or di-substituted with halogen of atomic number from 9 to 35, alkyl of 1 to 4 carbon atoms, alkoxy of 1 to 4 carbon atoms or alkylthio of 1 to 4 carbon atoms, in the form of the free base or in the form of a pharmaceutically acceptable acid addition salt thereof.

2. The compound of claim 1 which is 1,2,3,4,10,10a-hexahydro-2-isopropyl-5-phenylbenz[g]isoquinoline.

3. The compounds of claim 1 wherein $R_1$ is H, $R_2$ is H and $R_3$ is H.

4. The compound of claim 1 wherein $R_1$ is H, $R_2$ is —CH$_3$ and $R_3$ is H.

5. The compound of claim 1 wherein $R_1$ is H, $R_2$ is —CH$_3$ and $R_3$ is

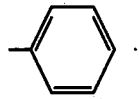

6. The compound of claim 1 wherein $R_1$ is H, $R_2$ is i—C$_3$H$_7$ and $R_3$ is —CH$_3$.

7. The compound of claim 1 wherein $R_1$ is H, $R_2$ is —CH$_3$ and $R_3$ is —CH$_3$.

8. The compound of claim 1 wherein $R_1$ is H, $R_2$ is —CH$_3$ and $R_3$ is C$_2$H$_5$.

9. The compound of claim 1 wherein $R_1$ is H, $R_2$ is —CH$_3$ and $R_3$ is

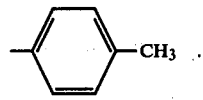

10. The compound of claim 1 wherein $R_1$ is H, $R_2$ is —CH$_3$ and $R_3$ is

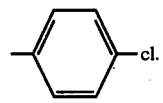

11. The compound of claim 1 wherein $R_1$ is H, $R_2$ is —CH$_3$ and $R_3$ is

12. The compound of claim 1 wherein $R_1$ is H, $R_2$ is i—$C_3H_7$ and $R_3$ is

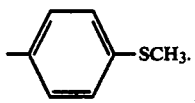

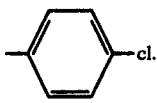

13. The compound of claim 1 wherein $R_1$ is H, $R_2$ is i—$C_3H_7$ and $R_3$ is H.

14. The compound of claim 1 wherein $R_1$ is 7-$CH_3$, $R_2$ is —$CH_3$ and $R_3$ is H.

15. The compound of claim 1 wherein $R_1$ is 7-$CH_3$, $R_2$ is H and $R_3$ is H.

16. A pharmaceutical composition for use in treating pain which comprises the step of administering to an animal in need of treatment an analgesic effective amount of a compound of claim 1, in association with a pharmaceutically acceptable diluent or carrier therefor.

17. A method of treating pain in animals which comprises the step of administering a therapeutically effective amount of a compound of claim 1 to an animal in need of such treatment.

* * * * *